(12) United States Patent
Elings et al.

(10) Patent No.: US 9,573,898 B2
(45) Date of Patent: Feb. 21, 2017

(54) PYRIDINE DERIVATES AND THEIR USE AS UMAMI TASTANTS

(71) Applicants: Jacob Antonius Elings, Huizen (NL); Cornelis Winkel, Bussum (NL); Stefan Michael Furrer, Cincinnati, OH (US)

(72) Inventors: Jacob Antonius Elings, Huizen (NL); Cornelis Winkel, Bussum (NL); Stefan Michael Furrer, Cincinnati, OH (US)

(73) Assignee: Givaudan S.A., Vernier (CH)

( * ) Notice: Subject to any disclaimer, the term of this patent is extended or adjusted under 35 U.S.C. 154(b) by 132 days.

(21) Appl. No.: 14/344,361

(22) PCT Filed: Sep. 20, 2012

(86) PCT No.: PCT/EP2012/068495
§ 371 (c)(1),
(2) Date: Mar. 12, 2014

(87) PCT Pub. No.: WO2013/041599
PCT Pub. Date: Mar. 28, 2013

(65) Prior Publication Data
US 2014/0342073 A1 Nov. 20, 2014

Related U.S. Application Data

(60) Provisional application No. 61/537,331, filed on Sep. 21, 2011.

(51) Int. Cl.
| | | |
|---|---|---|
| A23L 1/226 | (2006.01) |
| C07D 213/56 | (2006.01) |
| C07D 213/40 | (2006.01) |
| C07D 213/50 | (2006.01) |

(52) U.S. Cl.
CPC ......... *C07D 213/56* (2013.01); *A23L 27/2054* (2016.08); *A23L 27/88* (2016.08); *C07D 213/40* (2013.01); *C07D 213/50* (2013.01); *A23V 2002/00* (2013.01)

(58) Field of Classification Search
CPC ... C07D 213/40; C07D 213/50; C07D 213/56; A23L 27/2054; A23L 27/88; A23V 2002/00
USPC .................. 426/534, 536, 537, 650; 546/337
See application file for complete search history.

(56) References Cited

U.S. PATENT DOCUMENTS

| | | |
|---|---|---|
| 2004/0176595 A1 | 9/2004 | Dow et al. |
| 2005/0137245 A1 | 6/2005 | Hudkins et al. |
| 2010/0136136 A1 | 6/2010 | Galan et al. |

FOREIGN PATENT DOCUMENTS

| | | |
|---|---|---|
| WO | WO 2011/004016 A1 | 1/2011 |
| WO | WO 2011/095533 A1 | 8/2011 |

OTHER PUBLICATIONS

PCT/EP2012/068495—International Search Report, Nov. 22, 2012.
PCT/EP2012/068495—International Written Opinion, Nov. 22, 2012.
PCT/EP2012/068495—International Preliminary Report on Patentability, Mar. 25, 2014.
GB 1117235.0—Great Britain Search Report, Jan. 19, 2012.
Kitazawa, et al., "Studies on the synthesis of antiulcer agents, V. Synthesis and antiulcer activity of dihydrobenzofuranone derivatives", Yakugaku Zasshi, 1989, pp. 241-249, vol. 109, No. 4, Japan.
Kitazawa, et al., "Studies on the synthesis of antiulcer agents, VI. Synthesis and antiulcer activity of dihydrobenzofuranone derivatives", Yakugaku Zasshi, 1989, pp. 718-736, vol. 109, No. 10, Japan.
Yamaguchi, et al., "What is Umami?", Food Reviews International, 1998, pp. 123-138, vol. 14, Nos. 2 and 3, Marcel Dekker, Inc., New York, New York.
Database Registry [Online], Chemical Abstract Service, Columbus, Ohio, US; Jun. 18, 2002, XP 002686949, retrieved from STN Database accession No. 431927-97-8, abstract.
Database Registry [Online], Chemical Abstract Service, Columbus, Ohio, US; Jun. 20, 2002, XP 002686950, retrieved from STN Database accession No. 432533-21-6, abstract.
Database Registry [Online], Chemical Abstract Service, Columbus, Ohio, US; Oct. 29, 2009, XP 002686951, retrieved from STN Database accession No. 1190524-60-7, abstract.
Database Registry [Online], Chemical Abstract Service, Columbus, Ohio, US; Feb. 14, 2005, XP 002686947, retrieved from STN Database accession No. 830343-69-6, abstract.
Database Registry [Online], Chemical Abstract Service, Columbus, Ohio, US; Apr. 25, 2001, XP 002686948, retrieved from STN Database accession No. 332399-37-8, abstract.
Enamine Historical HTS Collection, CAS Registry No. 425400-06-2, Sep. 23, 2011, CHEMCATS Accession No. 0019098541.

*Primary Examiner* — Leslie Wong
(74) *Attorney, Agent, or Firm* — Curatolo Sidoti Co., LPA; Joseph G. Curatolo; Salvatore A. Sidoti

(57) ABSTRACT

Compounds of the formula (1) and their use as umami tastants:

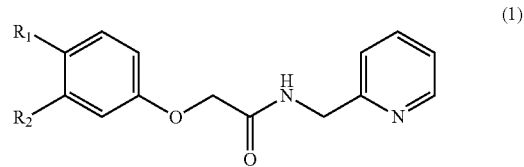

(1)

wherein
$R_1$ is chosen from Me, Et, Pr, or iPr,
$R_2$ is chosen from H or Me,
or $R_1$ and $R_2$ together with the aromatic ring carbon atoms, form a 5 or 6 membered ring.

15 Claims, No Drawings

PYRIDINE DERIVATES AND THEIR USE AS UMAMI TASTANTS

CROSS REFERENCE TO RELATED APPLICATIONS

This application is a national stage application of International Application No. PCT/EP2012/068495, filed 20 Sep. 2012, which claims priority from U.S. Provisional Patent Application No. 61/537,331, filed 21 Sep. 2011, from which applications priority is claimed, and which are incorporated herein by reference.

This disclosure relates to a novel molecule and its use in creating, enhancing or modifying umami flavour.

Umami is a flavour sensation generally associated with Asian cuisine. In addition, improved umami taste helps make low salt products more palatable. Umami flavour has traditionally been achieved by the addition of monosodium glutamate (MSG) to foodstuffs. However, the presence of MSG in foodstuffs is not universally acceptable, and there is an interest in the achievement of umami taste with lower proportions of MSG than is normally the case.

Compounds have now been found that, even despite their relatively low polarity and consequently their relatively low water solubility, leave a strong umami impression when placed in the mouth. By the use of these compounds, it is possible to create an acceptable umami impression in foodstuffs and beverages using low amounts of MSG, or even no MSG.

Provided in one aspect is a compound of the formula (1)

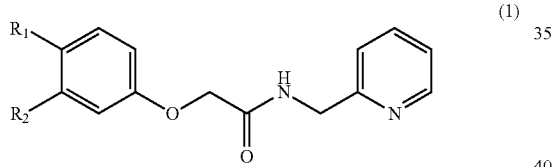

(1)

wherein,
$R_1$ is chosen from Me, Et, Pr, or iPr,
$R_2$ is chosen from H or Me,
or $R_1$ and $R_2$ together with the aromatic ring carbon atoms, form a 5 or 6 membered ring.

As used herein, Me is methyl, Et is ethyl, Pr is propyl, and iPr is isopropyl.

In another aspect of the invention there is provided a compound of formula (I) selected from the group consisting of:
2-[(2,3-dihydro-1H-indenyl-5-yl) oxy]-N-(pyridine-2-ylmethyl)acetamide;
2-[(5,6,7,8-tetrahydronaphthalen-2yl) oxy]-N-(pyridine-2-ylmethyl)acetamide;
2-(4-methylphenoxy)-N-(pyridin-2-ylmethyl)acetamide;
2-(4-ethylphenoxy)-N-(pyridin-2-ylmethyl)acetamide;
2-(4-propylphenoxy)-N-(pyridin-2-ylmethyl)acetamide;
2-(4-isopropylphenoxy)-N-(pyridin-2-ylmethyl)acetamide;
2-(3,4-dimethylphenoxy)-N-(pyridin-2-ylmethyl)acetamide;
2-(3-methyl,4-ethylphenoxy)-N-(pyridin-2-ylmethyl)acetamide;
2-(3-methyl,4-propylphenoxy)-N-(pyridin-2-ylmethyl)acetamide; and
2-(3-methyl,4-isopropylphenoxy)-N-(pyridin-2-ylmethyl)acetamide.

In a particular embodiment, the compound of formula (1) is 2-[(2,3-dihydro-1H-indenyl-5-yl) oxy]-N-(pyridine-2-ylmethyl)acetamide represented by the formula:

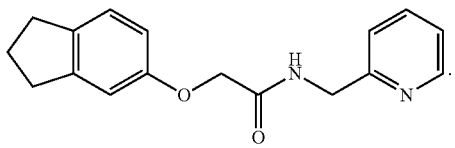 [SMILES: O=C(COc1ccc2c(c1)CCC2)NCc1ccccn1]

In another particular embodiment, the compound of formula (1) is 2-(4-ethylphenoxy)-N-(pyridin-2-ylmethyl)acetamide:

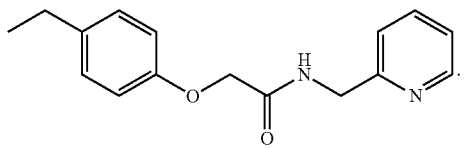 [SMILES: CCc1ccc(OCC(=O)NCc2ccccn2)cc1]

In yet another particular embodiment, the compound of formula (1) is 2-(4-isopropylphenoxy)-N-(pyridin-2-ylmethyl)acetamide:

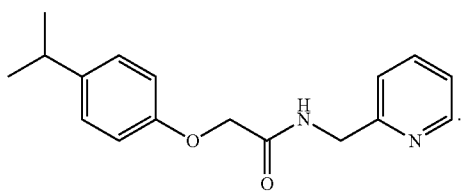 [SMILES: CC(C)c1ccc(OCC(=O)NCc2ccccn2)cc1]

In yet another aspect, the compound of formula (1) is 2-(3,4-dimethylphenoxy)-N-(pyridin-2-ylmethyl)acetamide:

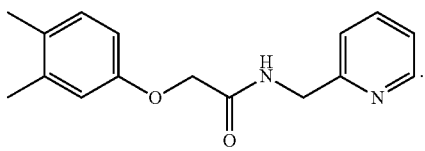 [SMILES: Cc1ccc(OCC(=O)NCc2ccccn2)cc1C]

In another particular embodiment of the invention there is provided a compound of formula (I), provided that it is not one or more of the compounds selected from:
2-[(2,3-dihydro-1H-indenyl-5-yl) oxy]-N-(pyridine-2-ylmethyl)acetamide;
2-(4-ethylphenoxy)-N-(pyridin-2-ylmethyl)acetamide;
2-(4-isopropylphenoxy)-N-(pyridin-2-ylmethyl)acetamide;
2-(3,4-dimethylphenoxy)-N-(pyridin-2-ylmethyl)acetamide; and
2-(3-methyl,4-isopropylphenoxy)-N-(pyridin-2-ylmethyl) acetamide.

The compounds of formula (1) may be prepared by methods well known to the art. One such method involves the preparation of the ether linkage first by reacting the appropriate alcohol with the bromo-acetic acid ethyl ester in the presence of a basic catalyst, followed by the amide bond formation by reacting the ester with the appropriate amine. The latter step can be improved when the ethanol is removed directly from the reaction.

The synthesis of compounds of formula (1) is explained in greater details in the examples set forth below.

Compounds of formula (1) can provide a strong umami impression even at quite low usage levels. As such, they may add taste to foodstuffs, beverages and oral care products, making them eminently suitable as a flavourant ingredient in these applications.

Accordingly, in another aspect there is provided a consumable composition comprising a compound of the formula (1).

In another aspect there is provided a method to confer, enhance, improve or modify the taste of a consumable composition, which method comprises adding to said composition a compound of formula (1).

The consumable composition may consist of a compound of the formula (1), or it may contain a compound of formula (1) in combination with one or more other ingredients.

Said one or more other ingredients may be selected from a carrier material, a flavour base or any other adjuvant useful in flavour formulations.

The term carrier materials as used herein refers to materials that may aid in the formulation of a compound of formula (1) or any other flavour ingredient that might be contained in the consumable composition. Such carrier materials may be used to encapsulate materials to affect the rate at which they are released from the consumable composition, or to protect them from a surrounding medium. They are neutral or practically neutral from a taste point of view, that is, the material does not significantly alter the taste of the flavour composition.

As carrier materials, one can mention capsules, solvents, surfactants, absorbents, gums, polymers or the like.

The term "flavour base" as used herein means a composition comprising at least one flavourant co-ingredient that is different from a compound of the formula (1).

Moreover, the co-ingredients may be used to impart aroma or taste or both. For example, such a co-ingredient, if it is to be considered as being a flavourant must be recognized by a person skilled in the art as being able to create, modify or enhance a flavour accord.

Specific examples of flavour co-ingredients may include but are not limited to natural flavours, artificial flavours, spices, seasonings, and the like. Exemplary flavouring co-ingredients include synthetic flavour oils and flavouring aromatics and/or oils, oleoresins, essences, distillates, and extracts derived from plants, leaves, flowers, fruits, and so forth, and a combination comprising at least one of the foregoing.

Exemplary flavour oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, and cassia oil; useful flavouring agents include artificial, natural and synthetic fruit flavours. Additional exemplary flavours imparted by a flavouring agent include a milk flavour, a butter flavour, a cheese flavour, a cream flavour, and a yogurt flavour; tea or coffee flavours, such as a green tea flavour, an oolong tea flavour, a tea flavour, a cocoa flavour, a chocolate flavour, and a coffee flavour; mint flavours, such as a peppermint flavour, a spearmint flavour, and a Japanese mint flavour; spicy flavours, such as an asafetida flavour, an ajowan flavour, an anise flavour, an angelica flavour, a fennel flavour, an allspice flavour, a cinnamon flavour, a chamomile flavour, a mustard flavour, a cardamom flavour, a caraway flavour, a cumin flavour, a clove flavour, a pepper flavour, a coriander flavour, a sassafras flavour, a savory flavour, a Zanthoxyli Fructus flavour, a perilla flavour, a juniper berry flavour, a ginger flavour, a star anise flavour, a horseradish flavour, a thyme flavour, a tarragon flavour, a dill flavour, a capsicum flavour, a nutmeg flavour, a basil flavour, a marjoram flavour, a rosemary flavour, a bayleaf flavour, and a wasabi (Japanese horseradish) flavour; a nut flavour such as an almond flavour, a hazelnut flavour, a macadamia nut flavour, a peanut flavour, a pecan flavour, a pistachio flavour, and a walnut flavour; alcoholic flavours, such as a wine flavour, a whisky flavour, a brandy flavour, a rum flavour, a gin flavour, and a liqueur flavour; floral flavours; and vegetable flavours, such as an onion flavour, a garlic flavour, a cabbage flavour, a carrot flavour, a celery flavour, mushroom flavour, and a tomato flavour.

A particular example of a flavour co-ingredient is an ingredient that also imparts an umami impression.

Particular examples of other umami compounds that are useful in this application are compounds (including salts thereof) according to Formula (2)

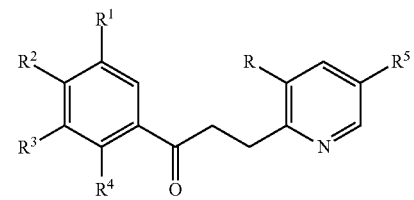

(2)

in which
  $R^1$ is selected from H, methyl or ethyl;
  $R^2$ is selected from H, OH, fluorine, $C_1$-$C_4$ linear or branched alkyl, or $C_1$-$C_6$ alkoxy wherein the alkyl group is linear or branched, or comprises or consists of a $C_3$-$C_5$ cycloalkyl moiety;
  $R^3$ is selected from H or methoxy;
  or $R^2$ and $R^3$ together form a bridging moiety —O—CH$_2$—O— between the phenyl carbon atoms to which they are connected;
  $R^4$ is selected from OH or methoxy; and
  $R^5$ and $R^6$ are independently selected from H or methyl;
  $R^1$, $R^2$, $R^3$, $R^4$, $R^5$ and $R^6$ being selected such that,
    (i) when $R^2$ and $R^3$ together form a bridging moiety —O—CH$_2$—O— between the phenyl carbon atoms to which they are connected, $R^1$, $R^5$, $R^6$ are H, and $R^4$ is OH; and
    (ii) when $R^4$ is OH and $R^1$-$R^3$ are H, at least one of $R^5$ or $R^6$ is methyl.

In a particular embodiment, $R^2$ is selected from H, OH, fluorine, methyl, or $C_1$-$C_6$ alkoxy wherein the alkyl group is linear or branched, or comprises or consists of a $C_3$-$C_5$ cycloalkyl moiety.

In a further particular embodiment, $R^2$ is selected from methyl, methoxy or isobutyloxy, $R^3$ is H, $R^4$ is OH and $R^5$ and $R^6$ are H.

Such compounds are described in UK patent application No. 0913804. Particular non-limiting examples of such compounds include:
1-(2-hydroxy-4,5-dimethylphenyl)-3-(pyridine-2-yl)propan-1-one;
1-(2-hydroxy-4-methylphenyl)-3-(pyridin-2-yl)propan-1-one;
1-(2-hydroxy-4-methoxyphenyl)-3-(pyridin-2-yl)propan-1-one; and 1-(2-hydroxy-4-isobutoxyphenyl)-3-(pyridine-2-yl)propan-1-one.

Other non-limiting examples of suitable compounds include:

N1-(2-methoxy-4-methylbenzyl)-N2-(2-pyridin-2-yl-ethyl) oxalamide;

N1-(2,4-dimethoxybenzyl)-N2-(2-pyridin-2-yl-ethyl) oxalamide;

N1-(2-methoxy-3-methylbenzyl)-N2-(2-(-5methyl)pyridin-2-yl-ethyl) oxalamide;

N-heptan-4-yl benzo(D)-1,3-dioxole 5-carboxamide;

N(3,7-dimethyl-2,6-octadien-1-yl) cyclopropyl carboxamide; and, cyclopropane carboxylic acid 2-isopropyl-5-methyl-cyclohexyl amide.

Other non-limiting examples of umami flavour-conferring and -enhancing compounds that may be used with a compound of formula (1) include MSG (mono sodium glutamate), IMP (inosine mono phosphate), GMP (guanosine mono phosphate) and those described in EP 1642886, WO 2005/015158, EP 1312268, WO 2003/088768, EP 1291342 and WO 2006/003107. Typical dosage levels for MSG are between 0.05% and 0.2%. Typical dosage levels for IMP/GMP are between 10 and 100 ppm.

The term "adjuvant" as used herein, means an ingredient that affects the performance of a composition, other than its hedonic performance. For example, an adjuvant may be an ingredient that acts as an aid to processing a composition or it may improve handling or storage of said composition. It might also be an ingredient that provides additional benefits such as imparting colour or texture to a composition. It might also be an ingredient that imparts light resistance or chemical stability to one or more ingredients contained in the composition. A detailed description of the nature and type of adjuvant commonly used in flavourant compositions cannot be exhaustive, but said ingredients are well known to a person skilled in the art. Examples of adjuvants include solvents and co-solvents; surfactants and emulsifiers; viscosity and rheology modifiers; thickening and gelling agents; preservative materials; pigments, dyestuffs and colouring matters; extenders, fillers and reinforcing agents; stabilisers against the detrimental effects of heat and light, bulking agents, acidulants, buffering agents and antioxidants.

The nature and type of the constituents of a consumable product do not warrant a more detailed description here, which in any case would not be exhaustive, the skilled person being able to select them on the basis of its general knowledge and according to the nature and the desired effect of said composition.

Consumable compositions may also include any solid or liquid composition that is consumed for at least one of nourishment and pleasure, or intended to be held in the mouth for a period of time before being discarded. A broad general list includes, but is not limited to, foodstuffs of all kinds, confectionery, baked goods, sweet goods, dairy products and beverages, and oral care products.

The proportions in which the compound of formula (1) can be incorporated into the various consumable compositions vary within a wide range of values. These values are dependent on the nature of the composition to be flavoured and on the desired organoleptic effect as well as the nature of the co-ingredients in a given flavour base when the compound is mixed with flavourant co-ingredients, solvents or additives commonly used in the art.

The proportion may vary between wide limits, typically between 0.1 ppm and 10 ppm by weight of a consumable composition, more particularly between 0.5 ppm and 5 ppm. However, these are general indications only of useful proportions, and the skilled flavourist may use proportions outside these ranges for particular effects.

In order to further illustrate the present embodiments and the advantages thereof, the following specific examples and comparative example are given, it being understood that same are intended only as illustrative and in no manner limitative.

Example 1

Synthesis of 2-(2,3-dihydro-1H-inden-5-yloxy)-N-(pyridin-2-ylmethyl)acetamide

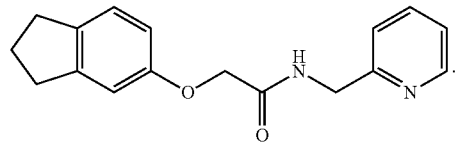 [SMILES: O=C(COc1ccc2c(c1)CCC2)NCc1ccccn1]

A mixture of 2,3-dihydro-1H-inden-5-ol (25 g, 186 mmol), ethyl 2-bromoacetate (31.1 g, 186 mmol) and potassium carbonate (25.8 g, 186 mmol) in acetone (80 ml) was stirred and heated under reflux for 4 hours. After cooling down the solid was removed by filtration and the filtrate diluted with 250 mL of ice/water and extracted three times with 100 mL of MBTE. The ethereal extracts were combined, washed successively with 1 N sodium hydroxide and water, and then dried over magnesium sulfate. After filtration, the solvent was removed under reduced pressure at a temperature of 60° C./20 mbar.

The remaining volatiles (starting materials) were removed under reduced pressure by using the Kugelrohr distillation unit till a maximum temperature of 140° C./7 mbar to yield 11 g of the intermediate compound.

In a 20 mL pear flask, ethyl 2-(2,3-dihydro-1H-inden-5-yloxy)acetate (2 g, 9.08 mmol) and pyridin-2-ylmethanamine (2 g, 18.49 mmol) were stirred at 120° C. for a few hours while ethanol was distilled off. Kugelrohr equipment was used.

The crude product was crystallized with diethyl ether/pentane, filtered and dried to yield 2 g of the title compound, purity >95%.

$^1$H-NMR in Chloroform-d: 2.02-2.10 (2H, quintet, C18), 2.80-2.92 (4H, m, C17, 19), 4.51-4.55 (2H, s, C11), 4.65-4.70 (2H, d, C7), 6.72-6.77 (1H, m, C15), 6.82-6.85 (1H, s, C21), 7.12-7.15 (1H, d, C14), 7.23-7.27 (1H, m, C4), 7.31-7.34 (1H, d, C3), 7.67-7.73 (1H, t, C5), 7.74-7.83 (1H, bs, —NH—), 8.55-8.59 (1H, d, C6)

Example 2

Two solutions were prepared:
A—a solution of 0.3% NaCl and 0.05% MSG,
B—a solution of 0.3% NaCl and 1 ppm of 2-(2,3-dihydro-1H-inden-5-yloxy)-N-(pyridin-2-ylmethyl)acetamide.

The samples were tasted by a professional panel composed of 2 women and 3 men aged between 30 and 60. The panel agreed that both solutions tasted umami. They also agreed that solution B was slightly stronger umami, had more succulence and sweetness and had more lingering notes.

Example 3

Two solutions were prepared:
A—a solution of 0.5% NaCl, 0.15% MSG and 0.025% Ribonucleotide mixture,
B—a solution of 0.5% NaCl, 0.05% MSG, 0.010% Ribonucleotide mixture and 2 ppm of 2-(2,3-dihydro-1H-inden-5-yloxy)-N-(pyridin-2- ylmethyl)acetamide.

The samples were tasted by a professional panel composed of 2 women and 3 men aged between 30 and 60. The panel agreed that both solutions were of equal umami strength.

Example 4

Three solutions were prepared:
A—a solution of 0.5% NaCl and 0.002% Ribonucleotide mixture,
B—a solution of 0.5% NaCl, 0.002% Ribonucleotide mixture and 10 ppm of 2-(4-ethylphenoxy)-N-(pyridin-2-ylmethyl)acetamide,
C—a solution of 0.5% NaCl, 0.002% Ribonucleotide mixture and 10 ppm of 2-(4-isopropylphenoxy)-N-(pyridin-2-ylmethyl)acetamide.

The samples were tasted by a professional panel composed of 2 women and 2 men aged between 30 and 60. The panel agreed that the solutions B and C were of stronger umami strength than solution A.

Example 5

A tomato soup mix was prepared from 9.4 g of sodium chloride, 1 g of mono sodium glutamate, 0.08 g ribonucleotides (ex yeast), 32 g of tomato powder (ex Spreda), 25.1 g of glucose, 21 g of starch (Ultrasperse® 5 ex National Starch), 5 g of palm fat powder, 3 g of yeast powder, 1 g of onion powder, 0.15 g of carrot powder, 0.05 g of ground white pepper, 0.3 g celery extract powder, 0.05 g of ground laurel leaf powder, and 1.85 g of sucrose.

25 g of the well mixed ingredients was added to 250 g of boiling water and stirred until completely dissolved.

The reference soup was compared with a batch of the same soup containing 2 ppm of 2-(2,3-dihydro-1H-inden-5-yloxy)-N-(pyridin-2-ylmethyl)acetamide.

A small group of flavourists (2 male, 2 female) tasted the soups and agreed that the test soup was more umami, and tasted more complex than the base soup.

Example 6

Plain potato chips were prepared.
One part was flavoured with 1.2% sodium chloride (sample A).
One part was flavoured with 1.2% sodium chloride and 0.3% mono sodium glutamate (sample B).
One part was flavoured with 1.2% sodium chloride and 5 ppm 2-(2,3-dihydro-1H-inden-5-yloxy)-N-(pyridin-2-ylmethyl)acetamide (sample C).

The samples A, B and C were tasted by a trained sensory panel composed of 20 women aged between 30 and 60.

The panel agreed that sample C was preferred over the other two samples.

Sample A was described as salty, sample B as salty and umami and sample C as salty, umami, long lasting, savory.

Example 7

Kikkoman® soy sauce was diluted 10 times with tap water. One part of the base soy sauce was taken as the reference. To another part (called sample A) 1.5 ppm of 2-(2,3-dihydro-1H-inden-5-yloxy)-N-(pyridin-2-ylmethyl)acetamide was added. To a third part (called sample B) 0.5 ppm of 2-(2,3-dihydro-1H-inden-5-yloxy)-N-(pyridin-2-ylmethyl)acetamide and 1 ppm of 1-(2-hydroxy-4-methoxyphenyl)-3-(pyridin-2-yl)propan-1-one were added.

A small group of flavourists (2 male, 2 female) tasted the diluted soy sauce and agreed that sample A and sample B were more umami and slightly more sweet. Both samples A and B were more complex than the base soy sauce, but sample B was clearly preferred over sample A.

Although the embodiments have been described in detail through the above description and the preceding examples, these examples are for the purpose of illustration only and it is understood that variations and modifications can be made by one skilled in the art without departing from the spirit and the scope of the disclosure. It should be understood that the embodiments described above are not only in the alternative, but can be combined.

The invention claimed is:

1. A consumable composition comprising a compound according to formula 1

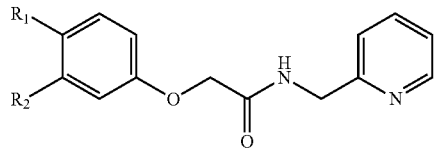

wherein $R_1$ is chosen from Me, Et, Pr, or iPr, $R_2$ is chosen from H or Me, or $R_1$ and $R_2$ together with the aromatic ring carbon atoms, form a 5 or 6 membered ring and the compound is selected from the group consisting of 2-(2,3-dihydro-1H-inden-5-yloxy)-N-(pyridin-2-ylmethyl)acetamide;

2-[(5,6,7,8-tetrahydronaphthalen-2yl) oxy]-N-(pyridine-2-ylmethyl)acetamide;

2-(4-propylphenoxy)-N-(pyridin-2-ylmethyl)acetamide;

2-(3-methyl,4-ethylphenoxy)-N-(pyridin-2-ylmethyl)acetamide;

2-(3-methyl,4-propylphenoxy)-N-(pyridin-2-ylmethyl)acetamide;

2-(4-methylphenoxy)-N-(pyridin-2-ylmethyl)acetamide;

2-(4-ethylphenoxy)-N-(pyridin-2-ylmethyl)acetamide;

2-(4-isopropylphenoxy)-N-(pyridin-2-ylmethyl)acetamide;

2-(3,4-dimethylphenoxy)-N-(pyridin-2-ylmethyl)acetamide; and 2-(3-methyl,4-isopropylphenoxy)-N-(pyridin-2-ylmethyl)acetamide; and, wherein the compound according to formula (1) is present to the extent of from between 0.1 ppm and 10 ppm, by weight of said consumable composition.

2. A method to confer, enhance, improve or modify the taste of a consumable composition, which method comprises adding to said composition the compound of formula (1)

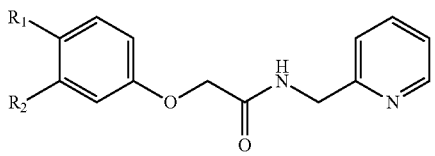

(1)

wherein
$R_1$ is chosen from Me, Et, Pr, or iPr,
$R_2$ is chosen from H or Me,
or $R_1$ and $R_2$ together with the aromatic ring carbon atoms, form a 5 or 6 membered ring and the compound is selected from the group consisting of
2-(2,3-dihydro-1H-inden-5-yloxy)-N-(pyridin-2-ylmethyl)acetamide;
2-[(5,6,7,8-tetrahydronaphthalen-2yl) oxy]-N-(pyridine-2-ylmethyl)acetamide;
2-(4-propylphenoxy)-N-(pyridin-2-ylmethyl)acetamide;
2-(3-methyl,4-ethylphenoxy)-N-(pyridin-2-ylmethyl)acetamide;
2-(3-methyl,4-propylphenoxy)-N-(pyridin-2-ylmethyl)acetamide;
2-(4-methylphenoxy)-N-(pyridin-2-ylmethyl)acetamide;
2-(4-ethylphenoxy)-N-(pyridin-2-ylmethyl)acetamide;
2-(4-isopropylphenoxy)-N-(pyridin-2-ylmethyl)acetamide;
2-(3,4-dimethylphenoxy)-N-(pyridin-2-ylmethyl)acetamide; and
2-(3-methyl,4-isopropylphenoxy)-N-(pyridin-2-ylmethyl)acetamide; and,
wherein the compound according to formula (1) is present to the extent of from between 0.1 ppm and 10 ppm, by weight of said consumable composition.

3. The consumable composition according to claim 1, which composition additionally comprises at least one compound and/or a salt thereof according to Formula (2)

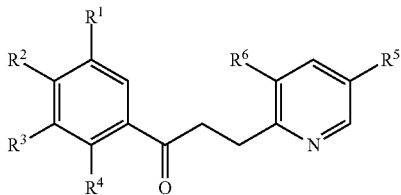

(2)

in which
$R^1$ is selected from H, methyl or ethyl;
$R^2$ is selected from H, OH, fluorine, $C_1$-$C_4$ linear or branched alkyl, or $C_1$-$C_6$ alkoxy wherein the alkyl group is linear or branched, or comprises or consists of a $C_3$-$C_5$ cycloalkyl moiety;
$R^3$ is selected from H or methoxy;
or $R^2$ and $R^3$ together form a bridging moiety —O—$CH_2$—O— between the phenyl carbon atoms to which they are connected;
$R^4$ is selected from OH or methoxy; and
$R^5$ and $R^6$ are independently selected from H or methyl;
$R^1$, $R^2$, $R^3$, $R^4$, $R^5$ and $R^6$ being selected such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and
(ii) when $R^4$ is OH and $R^1$-$R^3$ are H, at least one of $R^5$ or $R^6$ is methyl.

4. The consumable composition according to claim 1 in which a compound according to formula (1) is present to the extent of from between 0.5 ppm and 5 ppm, by weight of said consumable composition.

5. A consumable composition according to claim 3 in which a compound according to formula (1) is present to the extent of from between 0.5 ppm and 5 ppm, by weight of said consumable composition.

6. A consumable composition according to claim 1 wherein the compound is selected from the group consisting of
2-(2,3-dihydro-1H-inden-5-yloxy)-N-(pyridin-2-ylmethyl)acetamide and
2-[(5,6,7,8-tetrahydronaphthalen-2yl) oxy]-N-(pyridine-2-ylmethyl)acetamide.

7. The consumable composition according to claim 6, which composition additionally comprises at least one compound and/or a salt thereof according to Formula (2)

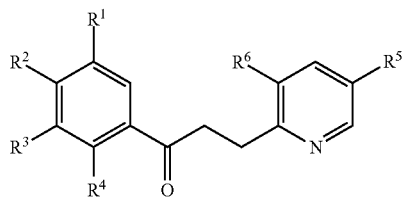

(2)

in which
$R^1$ is selected from H, methyl or ethyl;
$R^2$ is selected from H, OH, fluorine, $C_1$-$C_4$ linear or branched alkyl, or $C_1$-$C_6$ alkoxy wherein the alkyl group is linear or branched, or comprises or consists of a $C_3$-$C_5$ cycloalkyl moiety;
$R^3$ is selected from H or methoxy;
or $R^2$ and $R^3$ together form a bridging moiety —O—$CH_2$—O— between the phenyl carbon atoms to which they are connected;
$R^4$ is selected from OH or methoxy; and
$R^5$ and $R^6$ are independently selected from H or methyl;
$R^1$, $R^2$, $R^3$, $R^4$, $R^5$ and $R^6$ being selected such that,
(i) when $R^2$ and $R^3$ together form a bridging moiety —O—$CH_2$—O— between the phenyl carbon atoms to which they are connected, $R^1$, $R^5$, $R^6$ are H, and $R^4$ is OH; and
(ii) when $R^4$ is OH and $R^1$-$R^3$ are H, at least one of $R^5$ or $R^6$ is methyl.

8. The consumable composition according to claim 6 in which the compound according to formula (1) is present to the extent of from between 0.5 ppm and 5 ppm, by weight of said consumable composition.

9. The consumable composition according to claim 7 in which the compound according to formula (1) is present to the extent of from between 0.5 ppm and 5 ppm, by weight of said consumable composition.

10. The compound 2-[(5,6,7,8-tetrahydro naphthalen-2yl) oxy]-N-(pyridine-2-ylmethyl)acetamide.

11. The compound 2-(4-propylphenoxy)-N-(pyridin-2-ylmethyl)acetamide.

12. The compound 2-(3 methyl,4-ethyl phenoxy)-N-(pyridin-2-ylmethyl)acetamide.

13. The compound 2-(3-methyl,4-propyl phenoxy)-N-(pyridin-2-ylmethyl)acetamide.

14. The method of claim 2 wherein the compound is selected from the group consisting of
- 2-(2,3-dihydro-1H-inden-5-yloxy)-N-(pyridin-2-ylmethyl)acetamide and
- 2-[(5,6,7,8-tetrahydronaphthalen-2yl) oxy]-N-(pyridine-2-ylmethyl)acetamide.

15. The method of claim 2 in which a compound according to formula (1) is present to the extent of from between 0.5 ppm and 5 ppm, by weight of said consumable composition.

* * * * *